(12) United States Patent
Anderson et al.

(10) Patent No.: US 8,530,861 B1
(45) Date of Patent: Sep. 10, 2013

(54) DETECTABLY-LABELED CARBON FIBER

(75) Inventors: Kraig Anderson, Burlingame, CA (US); Angele Sjong, Louisville, CO (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/577,486

(22) PCT Filed: May 1, 2012

(86) PCT No.: PCT/US2012/035953
§ 371 (c)(1),
(2), (4) Date: Aug. 7, 2012

(51) Int. Cl.
*G01N 21/64* (2006.01)

(52) U.S. Cl.
USPC .................. 250/459.1; 250/458.1

(58) Field of Classification Search
USPC ...................................... 250/459.1
See application file for complete search history.

(56) References Cited

U.S. PATENT DOCUMENTS

| | | |
|---|---|---|
| 7,572,642 B2 | 8/2009 | Skinner et al. |
| 8,025,144 B2 | 9/2011 | Lewis et al. |
| 2002/0155490 A1 | 10/2002 | Skinner et al. |
| 2006/0180440 A1 | 8/2006 | Lewis et al. |
| 2007/0009894 A1 | 1/2007 | Crothers |
| 2009/0121121 A1 | 5/2009 | Dunleavy et al. |
| 2010/0021909 A1* | 1/2010 | Seul et al. ............ 435/6 |
| 2010/0167941 A1 | 7/2010 | Skinner et al. |
| 2011/0311505 A1 | 12/2011 | Ersoz et al. |

FOREIGN PATENT DOCUMENTS

| | | |
|---|---|---|
| EP | 1896820 A1 | 3/2008 |
| WO | WO 02/086148 A1 | 10/2002 |
| WO | WO2005021717 A2 | 3/2005 |
| WO | WO2007003883 A1 | 1/2007 |
| WO | WO2007133164 A1 | 11/2007 |
| WO | WO2011070402 A1 | 6/2011 |

OTHER PUBLICATIONS

International Search Report and Written Opinion for PCT/US2012/035953 dated Jul. 12, 2012.
Amemiya et al., Aminosilane multilayer formed on a single-crystalline diamond surface with controlled nanoscopic hardness and bioactivity by a wet process, *Langmuir* (Nov. 26, 2008), 25(1):203-209 (Abstract).
Bottini, Quantum-dot doped silica nanoparticles as probes for targeting of T-lymphocytes, *Int J Nanomedicine* (2007), 2(2):227-233.
Cao et al., Decoration of grapheme oxide sheets with luminescent rare-earth complexes, *Carbon* (Nov. 17, 2010), 49:1502-1507.
Ehlert et al., Carboxyl functionalization of carbon fibers through a grafting reaction that preserves fiber tensile strength, *Carbon* (Nov. 2011), 49(13):4246-4255 (Abstract).
Grotz et al., Sensing external spins with nitrogen-vacancy diamond, *New J. Phys.* (2011), 13:055004.

(Continued)

*Primary Examiner* — Marcus Taningco
(74) *Attorney, Agent, or Firm* — Pepper Hamilton LLP

(57) ABSTRACT

Compositions and methods for labeling carbon fiber with a detectable tag are disclosed. A composition includes at least one tag affixed to carbon fiber. The tag includes a plurality of detectable labels selected from quantum dots and organic fluorophores arranged in a detectable pattern. In addition, methods for the facile detection of the source, type, and/or physical condition of carbon fiber labeled with a detectable tag are disclosed.

25 Claims, 7 Drawing Sheets

(56) References Cited

OTHER PUBLICATIONS

Hernando et al., Immobilization of horseradish peroxidase via an amino silane on oxidized ultrananocrystalline diamond, *Diamond and Related Materials* (Jun. 23, 2006), 16:138-143.

Li et al., Functionalization of carbon nanofibers with diamine and polyimide oligmer, *Carbon* (2008), 46(8):1115-1125.

Liu et al., A switchable fluorescent quantum dot probe based on aggregation/disaggregation mechanism, *Chem. Commun.* (2011), 47:935-937.

Morgan, Carbon Fibers and Their Composites, CRC Press, Boca Raton, FL, (2005), pp. 403-405.

Plaseied et al., Influence of Carbon Nanofiber Content and Surface Treatment on the Mechanical Properties of Vinyl Ester, *Polymers and Polymer Composites* (2008), 16(7), 405-413.

Quian et al., Carboxyl-Functionalized and Bio-Conjugated Silica-Coated Quantum Dots as Targeting Probes for Cell Imaging, *J NanoSci Nanotech* (Mar. 2010), 10(3):1668-1675 (Abstract).

Ravindran, et al., Covalent Coupling of Quantum Dots to Multiwalled Carbon Nanotubes for Electronic Device Applications, *Nano Letters* (2003), 3(4):447-453.

Wang, et al., Highly Luminescent Organosilane-Functionalized Carbon Dots, *Advanced Functional Materials* (2011), 21:1027-1031.

Ward, The use of fluorescence markers to record prosthetic wear patterns, *J Audiov Media Med.* (Sep. 1996), 19(3):123-129 (Abstract).

Zhao et al., Formation of a carbon fiber/polyhedral oligomeric silsesquioxane/carbon nanotube hybrid reinforcement and its effect on the interfacial properties of carbon fiber/epoxy composites, *Carbon* (2011), 49:2624-2632.

Morgan, Carbon Fibers and their Composites: Guidelines for the design of equipment for carbon fiber plant, CRC Press (2005), pp. 403-405.

\* cited by examiner

DETECTABLY-LABELED CARBON FIBER

CLAIM OF PRIORITY

This application is a U.S. national stage filing under 35 U.S.C. §371 of International Application No. PCT/US2012/035953 filed May 1, 2012 entitled "DETECTABLY-LABELED CARBON FIBER", the teachings of which are hereby incorporated by reference herein.

BACKGROUND

Carbon fiber (also known as graphite fiber or carbon graphite) is a material comprising fibers, e.g. about 5-10 μm in diameter, and composed mostly of carbon atoms. The carbon atoms are bonded together in crystals that are more or less aligned parallel to the long axis of the fiber. The crystal alignment gives the fiber high strength-to-volume ratio, thus making it very strong for its size. Several thousand carbon fibers are twisted together to form a yarn, which may be used by itself or woven into a fabric.

The properties of carbon fibers, such as high flexibility, high tensile strength, low weight, high resistance, high temperature tolerance and low thermal expansion, make them very popular in aerospace, civil engineering, wind turbines, military, motorsports, sporting goods, and numerous other applications. They are often combined with other materials to form a composite. When combined with a plastic resin and wound or molded it forms carbon fiber reinforced plastic, which is a very high strength-to-weight, extremely rigid, although somewhat brittle material.

Carbon fiber is, however, relatively expensive when compared to other fibers, such as glass fibers or plastic fibers. Therefore, the potential to recycle and reuse carbon fiber is commercially valuable and important. At the same time, numerous physical conditions, such as age, mechanical damage, temperature, temperature variation, ultraviolet (UV) light exposure, humidity, humidity variation, and chemical exposure, can damage and weaken carbon fiber, rendering its recycling less desirable and its reuse less suitable. Accordingly, there remains a need for a simple labeling or tagging system for carbon fiber that enables the facile detection of potential damage and/or weakening, as well as the source and type of the fiber, in order to assess the suitability of such carbon fiber for recycling and reuse in a variation of applications.

SUMMARY

Presently disclosed are compositions and methods for labeling carbon fiber with a detectable tag, and methods for the facile detection of the source, type, and/or physical condition of carbon fiber labeled with a detectable tag. In one aspect, there is provided a composition comprising at least one tag affixed to carbon fiber, wherein the tag comprises a plurality of detectable labels selected from the group consisting of quantum dots and organic fluorophores arranged in a detectable pattern. In another aspect, there is provided a method for labeling carbon fiber, the method comprising: providing carbon fiber to be labeled; and contacting the carbon fiber with a plurality of detectable labels selected from the group consisting of quantum dots and organic fluorophores to covalently attach the detectable labels to the carbon fiber in a detectable pattern. In still another aspect, there is provided a method for monitoring a physical condition of carbon fiber comprising detecting the fluorescence signature of a tag affixed to the carbon fiber, wherein the fluorescence signature provides information about the physical condition of the carbon fiber.

DETAILED DESCRIPTION

Figure 1A:
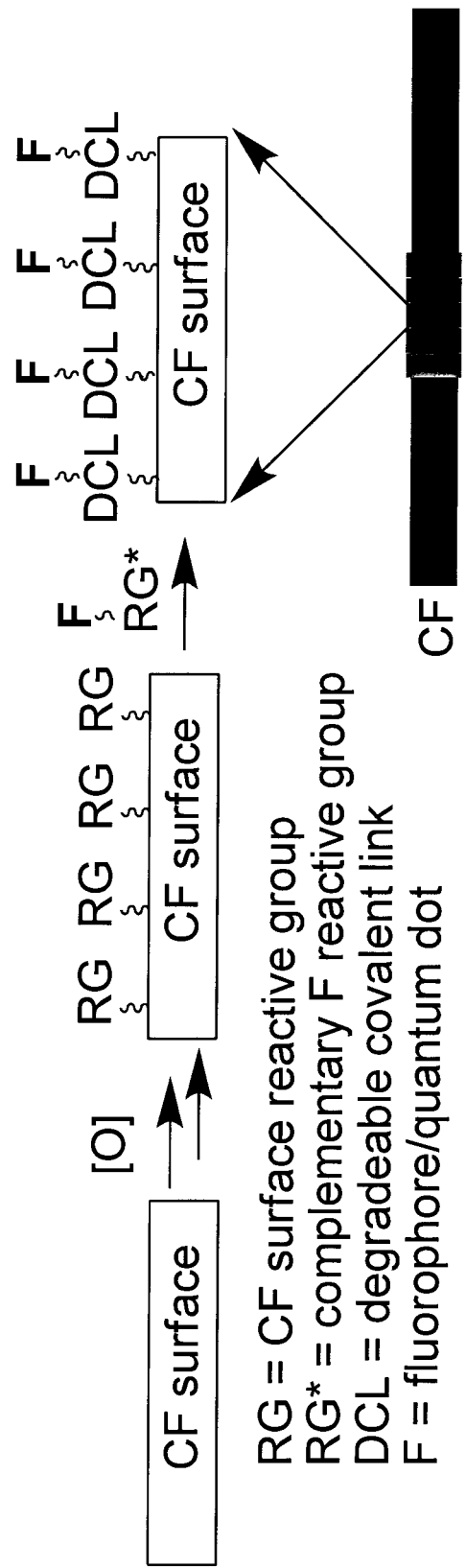
FIGS. 1A-1B are diagrams showing (A) representative reactive groups and covalent links between carbon fiber and fluorophores for an exemplary tag comprising five distinct colors in a band pattern, and (B) representative degradation of covalent bonds and/or fluorescent signature/strength for an exemplary tag leading to a decreased and/or blinking fluorescent signature over time.

Numerous physical conditions, such as age, mechanical damage, temperature, temperature variation, ultraviolet (UV) light exposure, humidity, humidity variation, and chemical exposure, can damage and weaken carbon fiber, rendering its recycling less desirable and its reuse less suitable. There is, therefore, a need for a simple labeling or tagging system for carbon fiber that enables the facile detection of potential damage and/or weakening, as well as source and/or type of the fiber, in order to assess the suitability of such carbon fiber for recycling and reuse in a variation of applications. The present disclosure provides such a system, including compositions and methods.

In one aspect, there is provided a composition comprising at least one tag affixed to carbon fiber, wherein the tag comprises a plurality of detectable labels selected from the group consisting of quantum dots and organic fluorophores arranged in a detectable pattern. The detectable pattern may comprise a plurality of different colored fluorescent shapes, for example two to five different colored fluorescent shapes, or more than five different colored fluorescent shapes. Any type of geometric shape may be suitably employed in the detectable pattern, including circles, dots, squares, triangles, rectangles, etc., and combinations of such shapes. In certain aspects, the detectable pattern employs bands. The type of shape and pattern selected are determined based on the number and type of quantum dots and/or fluorophores to be employed, and the number of desired pattern permutations.

In one aspect, the plurality of detectable labels is covalently attached to the carbon fiber. Covalent bonds may be formed via an amide, carbamide, ester, ether, or other suitable linking group. The covalent attachment is degradable by a physical condition, for example a condition selected from the group consisting of age, mechanical damage, temperature, temperature variation, ultraviolet (UV) light exposure, humidity, humidity variation, and chemical exposure. Changes in fluorescence behavior as a result of fluorophore bleaching, covalent link degradation, and/or the emergence of quantum dot blinking may be used to estimate age and condition of labeled fibers. With age, organic fluorophores may bleach and their covalent links may degrade. With quantum dots, individual or sparsely located quantum dots blink randomly as a function of areal density, but above a critical areal density, blinking is suppressed. Thus, as age or other conditions damage covalent links of attached quantum dots, the dots begin to blink, and as covalent links continue to age, the blinking frequency continues to change.

In another aspect, the tag is about 0.25 millimeter to about 1.0 millimeter long and comprises five or more distinct bands, or may comprise ten or more distinct bands. In an alternative aspect, the tag is more than about 1.0 millimeter long and comprises five or more distinct bands, or may comprise ten or more distinct bands. In yet another aspect, the detectable pattern may comprise a plurality of different colored fluorescent shapes arranged in a two-dimensional array.

Every instance of a tag can be made unique since the number of possible unique fluorescence tags can be made arbitrarily large simply by increasing the number of fluorescent shapes in a tag or the number of different colored fluorescent species. For example, a 1 mm tag using 10 different fluorescent species gives about $10^{12}$ (a trillion) unique tags; a 3 mm tag would give about $10^{36}$ unique tags. With a sufficiently large number of unique tags, no tag need be used more than once. Furthermore, the combination of multiple tags either on the same carbon fiber, or in a carbon fiber composite (e.g. plastic) article, the pattern of distinct tags located in any particular region provide a further unique and tamper-resistant "fingerprint" of that carbon fiber or article. A fiber source/type identification tag and a physical condition indicator tag may be placed at different locations on the carbon fiber, or a single location may serve as both identification tag and physical condition indicator tag.

A vast array of organic fluorophores and quantum dots functionalized for attachment to different groups are commercially available for fluorescent imaging. Organic fluorophores are available with groups (see "RG*" in FIG. 1A above) that are amine reactive (active esters, carboxylates, isothiocyanates, hydrazine), carboxyl-reactive (activated amines, carbodiimide), thiol-reactive (maleimides, acyl bromides, alkylsulfonothioates), azide-reactive (via alkyne click chemistry, glutaraldehydes) and others. Quantum dots are commercially available with surface groups that are amine-reactive (carboxylates), carboxy-reactive (amines), and alkoxylsilyl reactive (silanols on silica coated quantum dots). For example, several hundred different functionalized fluorophores and quantum dots are commercially available from Invitrogen (Carlsbad, Calif.), Sigma-Aldrich (St. Louis, Mo.), Biotium (Hayward, Calif.), Dyomics, GmbH (Jena, Germany), Thermo Fischer Scientific (Waltham, Mass.), and Interchim (San Diego, Calif.), among others.

Suitable quantum dots may include dots made from cadmium mercury telluride (CdHgTe), cadmium selenide (CdSe), cadmium selenide/zinc sulfide (CdSe/ZnS), cadmium sulfide (CdS), cadmium telluride (CdTe), cadmium telluride/cadmium sulfide (CdTe/CdS), and cadmium-free quantum dots, such as lead selenide (PbSe), lead sulfide (PbS), copper indium sulfide (CuInS), copper indium sulfide/zinc sulfide (CuInS/ZnS), or the like.

In addition to the great number of commercially available quantum dots, various types of functionalized quantum dots may be used, with various groups (see "RG*" in FIG. 1A above) suited for covalent attachment, e.g., amines, thiols, carboxylates, silyl esters, and more. For example, thiol-stabilized ZnS-capped CdSe quantum dots containing amine or thiol terminal groups; silica coated quantum dots functionalized with terminal amine or phosphate groups; silica coated quantum dots functionalized with carboxyl, amine, or thiol groups; and/or carbon quantum dots functionalized with silyl ethers may be used.

Figure 2A:
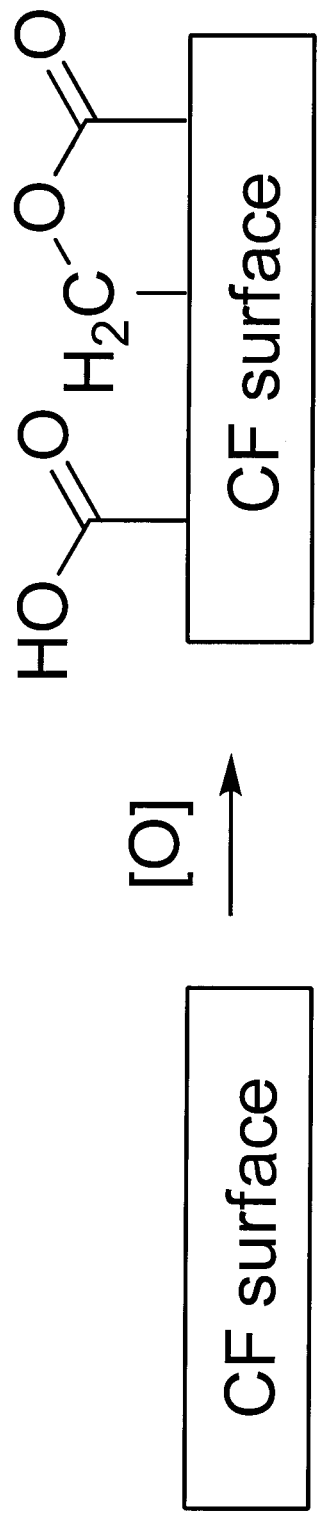
FIGS. 2A-2E are diagrams showing exemplary chemistries for steps that may be employed to affix desired fluorescent labels to carbon fiber: (A) Modification of the carbon fiber surface to include oxygenated surface reactive groups; (B) Conversion of oxygenated surface reactive groups to a single type of group (carboxyl) by hydrolysis and oxidation; (C) Conversion of oxygenated surface reactive groups to a single type of group (hydroxy) by reduction with borane gas ($BH_3$); (D) Further functionalization of a carboxy-terminated surface group with a secondary reactive group (1,3-diamino propane) to generate an amine surface reactive group; and (E) Further functionalization of a hydroxy-terminated surface group with a secondary reactive group (3-aminopropyl trimethoxysilane) to generate a silane surface reactive group.
Figure 2B:
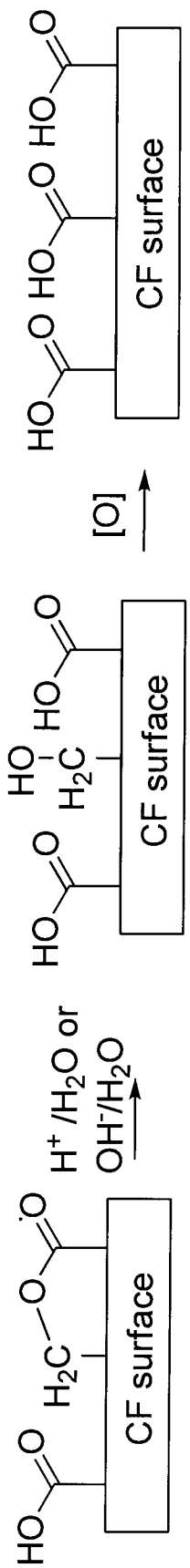

Moreover, any quantum dot with a silica shell can easily be functionalized with any of a number of alkyl thiols, alkyl carboxylates, alkyl halides, alkyl amines, alkyl glycydyl ethers, and the like that are coupled to a hydroxy-reactive trialkoxyl silyl group. Commercial sources of such chemicals include TCI America (Portland, Oreg.); Sigma-Aldrich (St. Louis, Mo.); and Chemical Land21 (Shanghai, China), among others. An exemplary reaction is described in FIG. 2(E), which also works with silanol-terminated surfaces. The choice of which colors of quantum dots to select (typically varying based on size for a particular quantum dot composition) and which type(s) of bond(s) one wishes to make between the functionalized quantum dot and the functionalized carbon fiber surface can be made based on the application for which the carbon fiber is being labeled.

Fluorescein isothiocyanate (FITC), a reactive derivative of fluorescein, has been one of the most common fluorophores chemically attached to other, non-fluorescent molecules to create new fluorescent molecules for a variety of applications. Other historically common fluorophores are derivatives of rhodamine (TRITC), coumarin, and cyanine Newer generations of fluorophores, many of which are proprietary, often perform better (more photostable, brighter, and/or less pH-sensitive) than traditional dyes with comparable excitation and emission.

Common generic dye families may include Xanthene derivatives (e.g. fluorescein, rhodamine, OREGON GREEN, eosin, TEXAS RED, CAL FLUOR dyes, eosins, phloxines, uranines, succineins, sacchareins, rosamines, rhodols, pyranines, anthraquinones, benzopyrans, thioxanthenes, perylene imides, phenanthridines, carbopyronins, and fluorescent proteins such as green fluorescent protein and yellow fluorescent protein); Cyanine derivatives (e.g. cyanine, indocarbocyanine, oxacarbocyanine, thiacarbocyanine, merocyanine, and QUASAR dyes); Naphthalene derivatives (e.g. dansyl and prodan derivatives); Coumarin derivatives; Oxadiazole derivatives (e.g. pyridyloxazole, nitrobenzoxadiazole and benzoxadiazole); Pyrene derivatives (e.g. CASCADE BLUE, etc.); Oxazine derivatives (e.g. Nile red, Nile blue, cresyl violet, oxazine 170, etc.); Acridine derivatives (e.g. proflavin, acridine orange, acridine yellow, etc.); Arylmethine derivatives (e.g. auramine, crystal violet, malachite green); and Tetrapyrrole derivatives (e.g. porphin, phtalocyanine, bilirubin), among others.

Common proprietary/trademarked dye families may include CYDYE (GE Healthcare); CF dye (Biotium); BODIPY (Invitrogen); ALEXA FLUOR (Invitrogen); DYLIGHT FLUOR (Thermo Scientific, Pierce); ATTO and TRACY (Sigma Aldrich); FLUOPROBES (Interchim); MEGASTOKES Dyes (Dyomics); SETA Dyes (SETA BioMedicals); SETAU Dyes (SETA BioMedicals); and SQUARE Dyes (SETA BioMedicals), among others. The choice of which colors of fluorophores to select and which type(s) of bond(s) one wishes to make between the functionalized fluorophore and the functionalized carbon fiber surface can be made based on the application for which the carbon fiber is being labeled. Many commercially available dyes include a suitable reactive group for attachment to the carboxylated carbon fiber surface, such as an amine or hydrazide group. Many of such dyes include a suitable amine reactive group, such as an activated carboxyl group.

In a certain aspect, the plurality of quantum dots may comprise quantum dots having an emission wavelength of about 450 nanometers to about 850 nanometers. In another aspect, the quantum dots may have an emission wavelength selected from the group consisting of 525 nanometers, 545 nanometers, 565 nanometers, 585 nanometers, 605 nanometers, 625 nanometers, 655 nanometers, 705 nanometers, and 800 nanometers.

In yet another aspect, the plurality of organic fluorophores may comprise fluorophores selected from the generic and/or proprietary dye families or specific fluorophores described above.

In another aspect, there is provided a method for labeling carbon fiber, the method comprising: providing carbon fiber to be labeled; and contacting the carbon fiber with a plurality of detectable labels selected from the group consisting of quantum dots and organic fluorophores to covalently attach the detectable labels to the carbon fiber in a detectable pattern. The detectable pattern may comprise a plurality of different colored fluorescent shapes, for example two to five different colored fluorescent shapes, or more than five different colored fluorescent shapes.

As noted above, the plurality of detectable labels are covalently attached to the carbon fiber. The covalent attachment is degradable by a physical condition, for example a condition selected from the group consisting of age, mechanical damage, temperature, temperature variation, ultraviolet (UV) light exposure, humidity, humidity variation, and chemical exposure.

In one aspect of the method, the tag is about 0.25 millimeter to about 1.0 millimeter long and comprises five or more distinct bands. In other aspects, the tag may comprise ten or more distinct bands, the tag is more than about 1.0 millimeter long and comprises five or more distinct bands, or the tag comprises ten or more distinct bands. The plurality of quantum dots may comprises quantum dots with specific emission wavelengths as described above, and the plurality of organic fluorophores may comprise fluorophores selected from the specific classes of dye derivatives described above.

In another aspect of the method, the covalent attachment is made by the steps of modifying the surface of the carbon fiber to include a plurality of primary oxygenated functional groups suitable for the attachment of detectable labels selected from the group consisting of functionalized quantum dots and functionalized organic fluorophores; converting the plurality of primary oxygenated functional groups to a single type of primary surface functional group; and contacting the primary surface functional group with a plurality of detectable labels selected from the group consisting of functionalized quantum dots and functionalized organic fluorophores, to yield covalent attachments between the primary surface functional group and the plurality of detectable labels.

In certain aspects, the primary oxygenated functional groups are selected from the group consisting of hydroxy groups, carboxy groups, esters, anhydrides, thiol, haloalkyl, and amino groups. The converting step may be accomplished by hydrolysis and oxidation to yield a carboxy-terminated primary surface functional group, or by reduction with borane gas ($BH_3$) to yield a hydroxy-terminated primary surface functional group. Alternatively, the converting step may be accomplished by reaction with isopropylidene malonate to graft terminal malonic esters to yield a carboxy-terminated primary surface functional group.

In another aspect of the method, the converting step further comprises functionalizing the primary surface functional group with a secondary functional group comprising a free reactive group, and wherein the contacting further comprises contacting the secondary functional group with the plurality of detectable labels, to yield covalent attachments between the secondary functional group and the plurality of detectable labels. The secondary functional group may be selected from the group consisting of a diamino alkane, an alkyl amine, an alkyl thiol, an alkyl carboxylate, an alkyl halide, an alkyl glycydyl ether, and a silane.

The fluorophores and/or quantum dots may be attached to the treated carbon fiber by any of the many covalent labeling methods known in biology and biochemistry for the use of such functionalized labels. For example, a convenient mode of attachment is through formation of an amide bond between an activated carboxy group on the carbon fiber surface and an amine or hydrazide-functionalized fluorophore. Commercially available amine-reactive fluorophores may also be first reacted with an excess of a polyfunctional amine such as 1,3 diaminopropane, and then coupled to an activated carboxy group on the carbon fiber surface.

Alternatively, the carbon fiber surface may be prepared to form an amide bond with fluorophores having an activated carboxyl group, first by activating the carboxy-carbon fiber surface, then reacting it with an excess of a polyfunctional amine such as 1,3 diaminopropane. The amine-terminated carbon fiber surface may then be coupled to fluorophores having a carboxyl or other amine reactive group.

In one example, the carboxyl-carbon fiber may be treated with a carbodiimide (e.g., 1-(3-dimethylaminopropyl)-3-ethylcarbodiimide, N,N'-N,N'-diisopropylcarbodiimide, N,N'-dicyclohexylcarbodiimide, or the like) to form a corresponding O-acylisourea, essentially an activated carboxyl ester. The activated O-acylisourea groups may then be reacted with amine or hydrazide substituted fluorophores to form an amide bond, for example by printing on the carbon fiber using an ink containing a solution of the desired amine or hydrazide substituted fluorophore and/or quantum dot.

In another example, the carboxyl-carbon fiber may be treated with a reagent such as norborane, p-nitrobenzoic acid, NHS (N-hydroxysuccinimide), and S—NHS (sulfo-N-hydroxysuccinimide). For example, activated NHS or S—NHS esters may be formed in a one step process by combining the carboxyl-carbon fiber, NHS or S—NHS, and a carbodiimide (e.g., 1-(3-dimethylaminopropyl)-3-ethylcarbodiimide, N,N'-N,N'-diisopropylcarbodiimide, N,N'-dicyclohexylcarbodiimide, or the like). The corresponding activated ester (e.g., an NHS or S—NHS ester) then may react with the desired amine or hydrazide substituted fluorophore and/or quantum dot.

In yet another aspect, the method further comprises the step detecting the detectable pattern in order to provide information about the physical condition of the carbon fiber. In another aspect the detectable pattern comprises a plurality of different colored fluorescent shapes arranged in a two-dimensional array.

Suitable chemistries for covalently affixing the tag/detectable labels typically begin with conventional carbon fiber surface treatments that are commonly used in the industry to place oxygenated groups at the carbon fiber surface, in order to improve non-covalent interactions with epoxy matrices compared to unmodified carbon fiber. These processes are then extended with further functionalization reactions known to work on unreactive carbon surfaces, such as diamond, and which have been used to attach groups and polymers such as polyimides, vinyl esters, and other elaborate structures to the surface of carbon fiber.

Generally, the surface of carbon fiber is modified to include reactive groups. A number of options are available for providing the surface of the carbon fiber with reactive groups suited for attachment of functionalized organic fluorophores and/or quantum dots (see "RG" in FIG. 1A above). Typical reactive groups which can be incorporated at the carbon fiber surface include carboxy, amino, hydroxyl, thiol, haloalkyl, and others. The oxygenated groups at the carbon fiber surface are then converted to a single type of group, e.g., carboxyl or hydroxyl. This can be done for just the segment to be labeled, or optionally the whole carbon fiber surface. The carboxy/hydroxyl groups may be further functionalized with other groups. The above hydroxyl and carboxyl groups may then be reacted directly with hydroxyl and carboxyl-reactive fluorophores (as described above) or may, optionally, be further functionalized to provide other reactive groups for reaction with available functionalized fluorophores.

Exemplary chemistries useful in the practice of the disclosed method are described in further detail in the Examples that follow below.

In still another aspect, there is provided a method for monitoring a physical condition of carbon fiber comprising detecting the fluorescence signature of a tag affixed to the carbon fiber, wherein the fluorescence signature provides information about the physical condition of the carbon fiber. In one aspect of the method, the tag comprises a plurality of detectable labels selected from the group consisting of quantum dots and organic fluorophores arranged in a detectable pattern. In another aspect, the detectable pattern comprises a plurality of different colored fluorescent shapes, and in another, the plurality of detectable labels is covalently attached to the carbon fiber.

In some aspects of the method, the physical condition may be selected from the group consisting of age, mechanical damage, temperature, temperature variation, ultraviolet (UV) light exposure, humidity, humidity variation, and chemical exposure. In another aspect, a change in the fluorescence signature relative to a control signature indicates a physical condition selected from the group consisting of age, mechanical damage, temperature, temperature variation, ultraviolet (UV) light exposure, humidity, humidity variation, and chemical exposure. In yet another aspect, the change is a decrease in either or both of the strength and blinking of the fluorescence signature relative to a control.

Monitoring quantum dot blinking, in addition to assessing at the strength of fluorescent signal, is desirable because the blinking provides its own control experiment, guarding against simple mechanical damage of a particular segment, which might leave a label with a dark patch that is uncorrelated to the age of the fiber. A calibration curve for age versus fluorescence behavior can be created for each type of quantum dot and covalent link using a series of accelerated aging experiments.

If tracking and authenticated history of the labeled carbon fiber is deemed important, e.g., in qualifying military or aviation parts, a manufacturer, or a manufacturing association or other standards body, can establish a registry of unique tags. Much the same process of centralized registry and assignment is now used to uniquely assign bar codes for retail products.

Obtaining carbon fiber (to be labeled) is well within the skill of those in the art. Briefly, each carbon filament is produced from a precursor polymer. The precursor polymer is commonly rayon, polyacrylonitrile (PAN) or petroleum pitch. For synthetic polymers such as rayon or PAN, the precursor is first spun into filaments, using chemical and mechanical processes to initially align the polymer atoms in a way to enhance the final physical properties of the completed carbon fiber. Precursor compositions and mechanical processes used during spinning may vary among manufacturers. After drawing or spinning, the polymer fibers are then heated to drive off non-carbon atoms (carbonization), producing the final carbon fiber. The carbon fibers may be further treated to improve handling qualities, then wound on to bobbins. Wound bobbins are then used to supply machines that produce carbon fiber threads or yarn.

A common method of manufacture involves heating the spun PAN filaments to approximately 300° C. in air, which breaks many of the hydrogen bonds and oxidizes the material. The oxidized PAN is then placed into a furnace having an inert atmosphere of a gas such as argon, and heated to approximately 2000° C., which induces graphitization of the material, changing the molecular bond structure. When heated in the correct conditions, these chains bond side-to-side (ladder polymers), forming narrow graphene sheets which eventually merge to form a single, columnar filament. The result is usually 93-95% carbon. Lower-quality fiber can be manufactured using pitch or rayon as the precursor instead of PAN. The carbon can become further enhanced, as high modulus, or high strength carbon, by heat treatment processes. Carbon heated to between 1500-2000° C. (carbonization) exhibits the highest tensile strength (820,000 psi, 5,650 MPa or $N/mm^2$), while carbon fiber heated from 2500 to 3000° C. (graphitizing) exhibits a higher modulus of elasticity (77,000,000 psi or 531 GPa or 531 $kN/mm^2$).

Carbon fiber filament yarns are used in several processing techniques: the direct uses are for prepregging, filament winding, pultrusion, weaving, braiding, etc. Carbon fiber yarn is rated by the linear density (weight per unit length, i.e. 1 g/1000 m=1 tex) or by number of filaments per yarn count, in thousands. For example, 200 tex for 3,000 filaments of carbon fiber is three times as strong as 1,000 carbon fibers, but is also three times as heavy. This thread can then be used to weave a carbon fiber filament fabric or cloth. The appearance of this fabric generally depends on the linear density of the yarn and the weave chosen. Some commonly used types of weave are twill, satin and plain. Carbon fibers can be also knitted or braided. Finished carbon fibers are available from a number of commercial manufacturers.

Fluorophores and/or quantum dots functionalized with reactive groups may be applied to the prepared carbon fiber by any means suitable for creating a detectable pattern of shapes. For example, the functionalized fluorophores and/or quantum dots may be suspended in a suitable fluid, such as water, to form an ink, which is then applied to the prepared carbon fiber using standard ink-jet printer technology. A modest ink-jet printer is readily capable of 300 DPI resolution, which permits printing about 12 distinct bands per millimeter on the carbon fiber. Alternatively, fluorophores and/or quantum dots may be applied by stamping, brushing, painting, solution exchange, or other suitable method of deposition, to create a desired, detectable pattern.

Fluorescence detection instruments are primarily of three types, each providing distinctly different information: Spectrofluorometers and microplate readers measure the average properties of bulk samples; Fluorescence microscopes resolve fluorescence as a function of spatial coordinates in two or three dimensions for microscopic objects (less than about 0.1 mm diameter); and Fluorescence scanners, including microarray readers, resolve fluorescence as a function of spatial coordinates in two dimensions for macroscopic objects. Other types of instrumentation that use fluorescence detection include capillary electrophoresis apparatus, DNA sequencers, microfluidic devices, and flow cytometers (which measure fluorescence per cell in a flowing stream, allowing subpopulations within a large sample to be identified and quantitated).

Recent advances in fluorescent imaging technology, for example as used in high-speed DNA microanalysis, fluorescent imaging microscopy, and other technologies, are readily capable of distinguishing fluorescent spots 1 micrometer (μm) in diameter at high signal to noise ratios. The ink-jet printer resolution mentioned above provides fluorescent bands about 90 micrometers wide, which is more than sufficient for ready detection and quantification of the fluorescent signal. A variety of suitable spectrofluorometer systems are commercially available, offered, for example, by Horiba Scientific, GoFoton, Life Technologies, Molecular Devices, Hitachi, and other suppliers.

The fluorescent signal will change with age depending on degradation of the covalent link between the fluorophore and/or quantum dot and the carbon fiber. Where organic fluorophores are used, bleaching of the fluorophore may also be correlated to age. Also, it is known that quantum dots emit continuously at high density, but blink at lower density. A series of accelerated aging experiments are conducted using elevated values of service conditions expected to be important, e.g., temperature, temperature variation, UV irradiation, humidity, chemical exposure, and so on.

The precise accelerated aging conditions will be dependent on a particular material and its expected service conditions, so some experimentation is unavoidable. However, such experimentation is already conducted at large scale for industrial materials, composites, and coatings, including carbon composite articles, so existing accelerated aging protocols would only need to be adapted to incorporate quantitative fluorescence imaging of the tags.

Once the fluorescence imaging data is collected as a function of time and conditions, the data can be fit using a parameterized set of differential equations which represent the various observed processes, e.g., photo-bleaching, cleavage of the degradable covalent links (see "DCL" in FIG. 1A above), etc. These can be correlated to any existing time-dependent descriptions of carbon fiber or composite article aging. The collection of these differential equations and their numerically fit parameters along with the existing time-dependent descriptions of carbon fiber and composite article aging is a model that correlates changes in quantitative fluorescence imaging data with aging changes in the carbon fiber (or composite). Consequently, once the model has been created, one simply needs to quantitatively measure a particular fluorescence tag and enter the data into the model to obtain an estimate of aging of the carbon fiber or composite article being examined.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into sub-ranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

EXAMPLES

Example 1

Production of Carbon Fiber Labeled with Quantum-Dot 5-Band Tag

Carbon fiber is obtained from a commercial source/supplier (e.g. Fibre Glast Developments Corporation (Brookville, Ohio) or Zoltek, Inc. (St. Louis, Mo.)). The surface of the carbon fiber is first modified to include oxygenated surface groups. The surface may be connected as the anode in an electrolytic process and functionalized with oxygenated surface groups such as hydroxy, carboxy, esters, anhydrides, etc. (see FIG. 2A). This is currently standard practice in the carbon fiber industry, and is currently used on all carbon fiber to improve adhesion to the matrix in carbon fiber reinforced plastic composites.

The oxygenated groups at the carbon fiber surface may next be converted to, or enriched for, a single type of chemical group. The complex mixture of oxygenated groups at the surface may be hydrolyzed and oxidized, which results in a substantially-enriched carboxy-terminated surface (see FIG. 2B). The surface may alternatively be partially converted or enriched, resulting in a mixture of types of chemical groups at the carbon fiber surface.

Figure 2C:
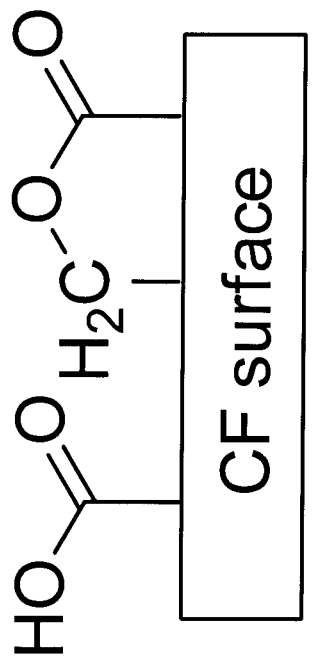
Figure 2C:
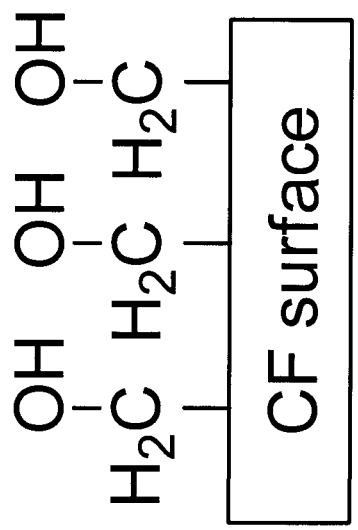

Alternatively, the complex mixture of oxygenated groups at the carbon fiber may be reduced, e.g., using borane gas ($BH_3$), which results in a hydroxy terminated surface (see FIG. 2C). As another alternative, naturally occurring hydroxy groups, e.g., those remaining from the first step of FIG. 2B above, or after FIG. 2C above, may be reacted with isopropylidene malonate to graft terminal malonic esters, effectively creating a carboxyl functionalized surface without the use of oxidation (as in the second step of FIG. 2B above).

In the case of carboxyl functionalized carbon fiber, five different colors of functionalized quantum dots are obtained from a commercial vendor, for example Qdot (525 ITK, 545 ITK, 565 ITK, 585 ITK, and 605 ITK) Amino (PEG) Quantum Dots 8 μm solution (Life Technologies Inc., U.S.A.). These functionalized quantum dots may be covalently bound to the carboxyl functionalized carbon fiber using 1-Ethyl-3-(3-Dimethylaminopropyl) carbodiimide, Hydrochloride (EDAC). Protocols for crosslinking molecules with this reagent may be known to those of ordinary skill in the art.

The five colors of functionalized quantum dots are solubilized with EDAC to form an ink and then printed on/applied to the carboxyl functionalized carbon fiber using an ink-jet printer capable of 300 DPI resolution (which permits printing about 12 distinct bands per millimeter on the carbon fiber). A generalized inkjet printer protocol suitable for deposition of the solubilized quantum dots may be employed to deposit each color of quantum dot in a distinct band to create a 5-band detectable tag. FIG. 1A illustrates an exemplary 5-band tag, bordered by continuous dark regions of the carbon fiber adjacent to the fluorescent tag.

Figure 2D:
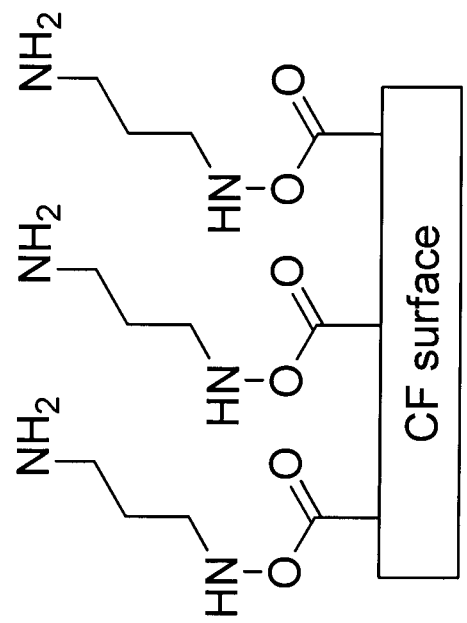
Figure 2D:
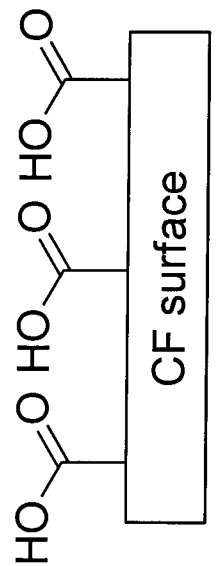
Figure 2E:
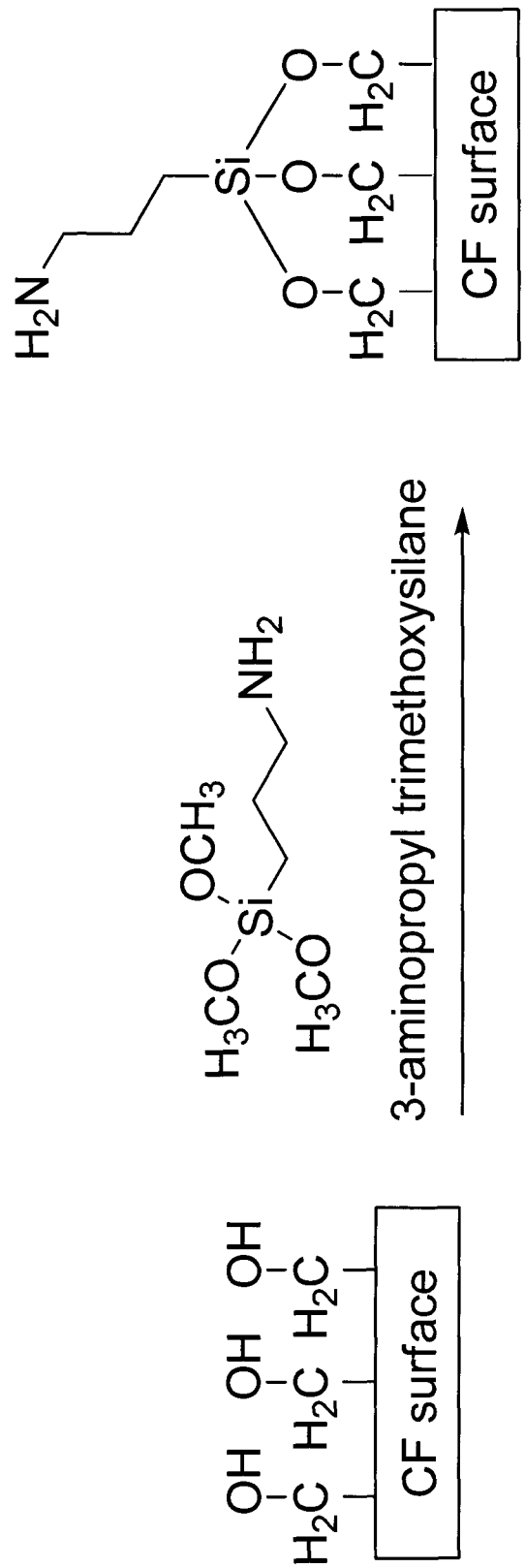

An optional protocol is to further functionalize the carboxy or hydroxyl groups at the carbon fiber surface prior to reaction with the functionalized fluorophore as described above. In such a step, the carboxy-terminated surface may be reacted with an amine coupled to another functional group, e.g. a diamino alkane (as shown in FIG. 2D), or an alkyl amine having another terminal reactive group, such as thiol, alkyne, etc. This results in formation of an amide bond between one amine and the carboxyl groups at the surface, leaving the other reactive group free (here, an amine).

Alternatively, the hydroxyl-terminated surface may be reacted with one or more ether forming reactions to result in the desired functional group. One example is to react the hydroxylated carbon fiber surface with functionalized trialkoxy silyl compounds, thus resulting in a monolayer of the selected functional group at the carbon fiber surface. A large number of alkyl thiols, alkyl carboxylates, alkyl halides, alkyl amines, alkyl glycydyl ethers, and so on that are coupled to a hydroxy-reactive trialkoxyl silyl group are commercially available (e.g., from TCI America (Portland, Oreg.); Sigma-Aldrich (St. Louis, Mo.); and Chemical Land21 (Shanghai, China), among others). Specific examples of functionalized silanes include 3-aminopropyl trimethoxysilane [13822-56-5], ((6-aminohexyl)aminomethyl)triethoxysilane [15129-36-9], and diethylaminomethyltriethoxysilane [15180-47-9], the latter of which is shown in the exemplary functionalization depicted in FIG. 2E.

As another alternative, 2-(N-heterocyclyloxy)uronium salts (e.g. O—(N-succinimidyl) N,N,N',N'-tetramethyluronium tetrafluoroborate (TSTU)) may be used to form NHS esters. Carboxyl-carbon fiber may be contacted with a solution of 0.1 M TSTU and 0.1M organic base (e.g., 2,6-dimethylaminopyridine) in a polar organic solvent (e.g., dimethyl formamide, dioxane, etc.). The reaction may be run for an hour at room temperature, and then the NHS ester-carbon fiber may be washed. The solvent and excess reagent removed may be recycled. The corresponding activated ester (e.g., an NHS or S—NHS ester) is then reacted with the desired amine or hydrazide substituted quantum dot (or other fluorophore).

Example 2

Detection of Aged Carbon Fiber Labeled with Detectable Tag

The fluorescence signature of carbon fiber, previously labeled with a detectable fluorescent tag (e.g. a 5-band quantum dot tag) substantially as described in Example 1 above, is examined in order to assess the age of such fiber and its suitability of recycling such carbon fiber. The fluorescence color, intensity, and potential quantum dot blinking of/in the tag are assessed to determine the age (and potential existence of physical damage) to the carbon fiber.

The current fluorescence signature of the tag is determined by using a commercially available fluorescence spectrophotometer (e.g. a Hitachi F-7000 system). The fluorescent color, intensity, and/or signal blinking of each distinct colored band in the tag is assessed to yield individual band data as well as a composite fluorescent signature for the entire tag (comprising 5 distinct bands, each comprising a different colored quantum dot label).

Figure 1B:
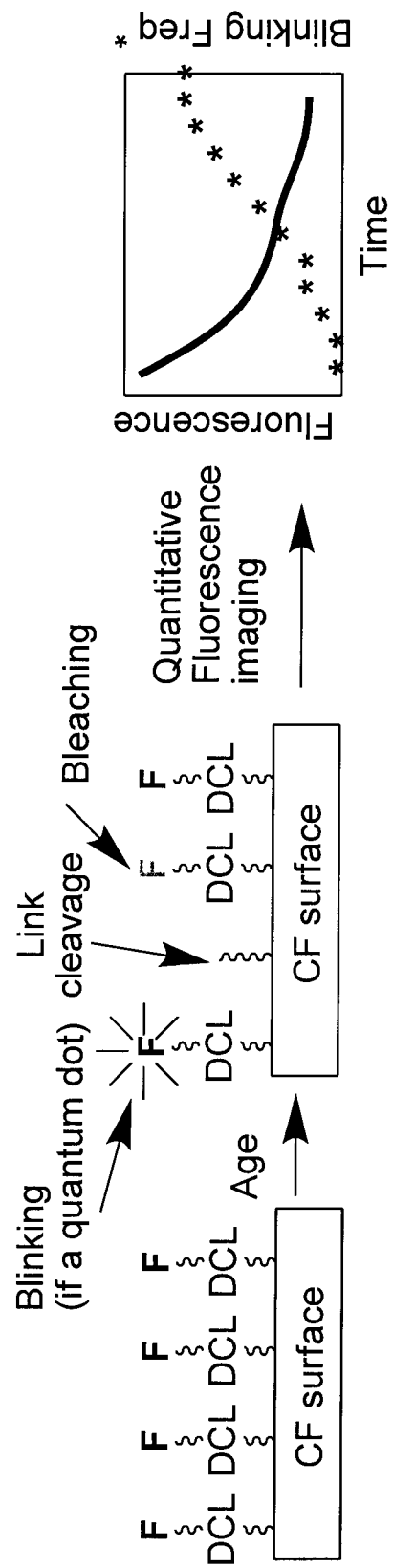

The current fluorescence signature of the tag is then compared to a control fluorescence signature obtained when the carbon fiber was first labeled with the tag. Comparison of current signature and control signature will identify any detectable changes to the fluorescent signature, whether reduction in color pattern, intensity, and/or signal blinking for one or more individual bands within the tag or for the composite tag as a whole. Such fluorescence signature change is indicative of the age (and/or potential physical damage to) the carbon fiber, manifested by cleavage/degradation of covalent bonds attaching the quantum dots to the carbon fiber, or by signal bleaching. See FIG. 1B for a schematic representation of carbon fiber aging and plotting of label fluorescence intensity and blinking versus time.

Example 3

Carbon Fiber Labeled with A Unique Tag to Aid in Tracking

A unique tag may be affixed to carbon fiber if tracking and authenticated history is deemed important, e.g., in qualifying military or aviation parts. A manufacturer, or a manufacturing association, or other standards body, may establish a registry of unique tags, similar to how centralized registry and assignment is currently used to uniquely assign bar codes for retail products.

Carbon fiber may be detectably-labeled with a unique tag in compliance with the United States Department of Defense Code 39 barcode requirements for marking all products sold to the United States military. This system is known as Logistics Applications of Automated Marking and Reading Symbols (LOGMARS).

Code 39 (also known as Alpha39, Code 3 of 9, Code 3/9, Type 39, USS Code 39, or USD-3) is a variable length, discrete barcode symbology. The Code 39 specification defines 43 characters, consisting of uppercase letters (A through Z), numeric digits (0 through 9) and a number of special characters (-, ., $, /, +, %, and space). An additional character (denoted '*') is used for both start and stop delimiters. Each character is composed of nine elements: five bars and four spaces. Three of the nine elements in each character are wide (binary value 1), and six elements are narrow (binary value 0). The width ratio between narrow and wide can be chosen between 1:2 and 1:3.

The barcode itself does not contain a check digit, but it can be considered self-checking on the grounds that a single erroneously interpreted bar cannot generate another valid character. However, Code 39 is still widely used and can be decoded with virtually any barcode reader. One advantage of Code 39 is that since there is no need to generate a check digit, it can easily be integrated into existing printing system by adding a barcode font to the system or printer and then printing the raw data in that font.

Carbon fiber for a military application, e.g. fiber/epoxy parts for fighter aircraft, are detectably labeled with a unique tag substantially as described in Example 1 above. For example, the unique code XYZ66D0109 may be catalogued by the Department of Defense central barcode registry as indicating carbon fiber manufactured by XYZ Corporation, part number 66D, in January (01) of 2009 (09). A detectable tag comprising this unique ten character barcode may be generated in 2-color fluorescence, for example by using red and blue quantum dots, according to the Code 39 symbology.

Upon shipment and delivery of the manufactured carbon fiber part to the military, the detectable label may be read, substantially as described in Example 2 above, and the tag code matched against a centralized code registry, to confirm that carbon fiber part is the correct part, manufactured from the correct manufacturer, on the correct date.

Example 4

Confirmation of a Uniquely-Labeled Carbon Fiber Lot

The detectable label affixed to a carbon fiber article may also facilitate comparison of two different manufactured lots of that article to distinguish a lot from an approved manufacturer from a lot sourced from an unknown or unapproved manufacturer.

Carbon fiber is obtained and detectably-labeled with a unique tag substantially as described in Example 1 above. An approved manufacturer of such carbon fiber may employ a detectable fluorescent tag that conveys the name of the manufacturer, the lot number, and date of manufacture. For example, the code 1208AAA00234 might convey a manufacture date of December (12) 2008 (08) by AAA Incorporated and lot #00234.

A two-dimensional, square detectable fluorescent tag corresponding to this code (which will be entered into a centralized computer registry, for example maintained by the purchaser of the carbon fiber) may, for example, comprise of three different colored quantum dots. The arrangement of those three colors in the upper left quadrant of the tag can convey the manufacturer confirmation. The arrangement in the upper right hand quadrant of the tag can convey manufacture date, and the arrangement in the lower left hand quadrant can convey the lot number of the carbon fiber.

A purchaser of carbon fiber lots from multiple different manufacturers may then detect the tag, substantially according to Example 2 above, in order to readily identify and confirm those lots that bear the unique detectable tag from those lots that do not.

What is claimed is:

1. A composition comprising at least one tag affixed to carbon fiber, wherein the tag is about 0.25 millimeter to about 1.0 millimeter long and comprises a plurality of detectable labels selected from the group consisting of quantum dots and organic fluorophores arranged in a detectable pattern.

2. The composition of claim 1, wherein the detectable pattern comprises a plurality of different colored fluorescent shapes.

3. The composition of claim 1, wherein the tag comprises five or more distinct bands.

4. The composition of claim 3, wherein the tag comprises ten or more distinct bands.

5. The composition of claim 1, wherein the tag is more than about 1.0 millimeter long and comprises five or more distinct bands.

6. The composition of claim 5, wherein the tag comprises ten or more distinct bands.

7. The composition of claim 1, wherein the detectable pattern comprises a plurality of different colored fluorescent shapes arranged in a two-dimensional array.

8. The composition of claim 1, wherein the plurality of quantum dots comprises quantum dots having an emission wavelength in the range of about 450 nanometers to about 850 nanometers.

9. The composition of claim 1, wherein the plurality of organic fluorophores comprises fluorophores selected from the group consisting of xanthene derivatives, cyanine derivatives, naphthalene derivatives, coumarin derivatives, oxadiazole derivatives, pyrene derivatives, oxazine derivatives, acridine derivatives, arylmethine derivatives, and tetrapyrrole derivatives.

10. A method for labeling carbon fiber, the method comprising:
   providing carbon fiber to be labeled; and
   contacting the carbon fiber with a plurality of detectable labels selected from the group consisting of quantum dots and organic fluorophores to covalently attach the detectable labels to the carbon fiber in a detectable pattern, wherein the detectable pattern is about 0.25 millimeter to 1.0 millimeter long.

11. The method of claim 10, wherein the detectable pattern comprises a plurality of different colored fluorescent shapes.

12. The method of claim 10, wherein the detectable pattern comprises five or more distinct bands.

13. The method of claim 12, wherein the detectable pattern comprises ten or more distinct bands.

14. The method of claim 10, wherein the detectable pattern is more than about 1.0 millimeter long and comprises five or more distinct bands.

15. The method of claim 14, wherein the detectable pattern comprises ten or more distinct bands.

16. The method of claim 10, wherein the plurality of quantum dots comprises quantum dots having an emission wavelength in the range of about 450 nanometers to about 850 nanometers.

17. The method of claim 10, wherein the plurality of organic fluorophores comprises fluorophores selected from the group consisting of xanthene derivatives, cyanine derivatives, naphthalene derivatives, coumarin derivatives, oxadiazole derivatives, pyrene derivatives, oxazine derivatives, acridine derivatives, arylmethine derivatives, and tetrapyrrole derivatives.

18. The method of claim 10, further comprising the step detecting the detectable pattern in order to provide information about the physical condition of the carbon fiber.

19. The method of claim 10, wherein the detectable pattern comprises a plurality of different colored fluorescent shapes arranged in a two-dimensional array.

20. A method for monitoring a physical condition of carbon fiber comprising the step of detecting the fluorescence signature of a tag affixed to the carbon fiber, wherein the tag is about 0.25 millimeter to about 1.0 millimeter long and wherein the fluorescence signature provides information about the physical condition of the carbon fiber.

21. The method of claim 20, wherein the tag comprises a plurality of detectable labels selected from the group consisting of quantum dots and organic fluorophores arranged in a detectable pattern.

22. The method of claim 21, wherein the detectable pattern comprises a plurality of different colored fluorescent shapes.

23. The method of claim 20, wherein the physical condition is selected from the group consisting of age, mechanical damage, temperature, temperature variation, ultraviolet (UV) light exposure, humidity, humidity variation, and chemical exposure.

24. The method of claim 20, wherein a change in the fluorescence signature relative to a control signature indicates a physical condition selected from the group consisting of age, mechanical damage, temperature, temperature variation, ultraviolet (UV) light exposure, humidity, humidity variation, and chemical exposure.

25. The method of claim 24, wherein the change is a decrease in either or both of the strength and blinking of the fluorescence signature relative to a control.

* * * * *

UNITED STATES PATENT AND TRADEMARK OFFICE
CERTIFICATE OF CORRECTION

PATENT NO.        : 8,530,861 B1
APPLICATION NO.   : 13/577486
DATED             : September 10, 2013
INVENTOR(S)       : Anderson et al.

Page 1 of 1

It is certified that error appears in the above-identified patent and that said Letters Patent is hereby corrected as shown below:

In the Specification

In Column 4, Line 25, delete "cyanine" and insert -- cyanine. --, therefor.

In Column 4, Line 32, delete "eosins," and insert -- eosines, --, therefor.

In Column 4, Line 47, delete "phtalocyanine" and insert -- phthalocyanine --, therefor.

Signed and Sealed this
Eighth Day of April, 2014

Michelle K. Lee
*Deputy Director of the United States Patent and Trademark Office*